United States Patent
Lattner et al.

(10) Patent No.: US 8,399,727 B2
(45) Date of Patent: Mar. 19, 2013

(54) PRODUCTION OF PARA-XYLENE BY THE METHYLATION OF BENZENE AND/OR TOLUENE

(75) Inventors: James R. Lattner, La Porte, TX (US); Mark P. Hagemeister, Houston, TX (US); Christopher Gordon Smalley, Manassas, VA (US); Jon Edmond Randolph Stanat, Westhampton Beach, NY (US); Timothy Paul Bender, Houston, TX (US); Masaaki Sugita, McLean, VA (US); Rathna P. Davuluri, Fairfax, VA (US); Lu Han, Herndon, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 311 days.

(21) Appl. No.: 12/899,193

(22) Filed: Oct. 6, 2010

(65) Prior Publication Data

US 2011/0092756 A1    Apr. 21, 2011

Related U.S. Application Data

(60) Provisional application No. 61/253,745, filed on Oct. 21, 2009.

(51) Int. Cl.
*C07C 2/66* (2006.01)

(52) U.S. Cl. .................... 585/467; 585/469; 585/903

(58) Field of Classification Search .................. 585/467, 585/469, 903
See application file for complete search history.

(56) References Cited

U.S. PATENT DOCUMENTS

| | | |
|---|---|---|
| 4,067,920 A | 1/1978 | Kaeding |
| 5,491,277 A | 2/1996 | Stine et al. |
| 5,939,597 A | 8/1999 | Dessau et al. |
| 6,172,274 B1 | 1/2001 | Gosling |
| 6,504,072 B1 | 1/2003 | Brown et al. |
| 6,642,426 B1 | 11/2003 | Johnson et al. |
| 2002/0151758 A1 | 10/2002 | Das et al. |
| 2004/0158111 A1 | 8/2004 | Johnson et al. |
| 2005/0070749 A1 | 3/2005 | Ghosh et al. |
| 2005/0075524 A1 | 4/2005 | Feng et al. |

FOREIGN PATENT DOCUMENTS

WO    2004/074219    9/2004

*Primary Examiner* — Thuan D Dang
(74) *Attorney, Agent, or Firm* — Andrew B. Griffis

(57) ABSTRACT

In a process for the production of para-xylene, an aromatic feedstock comprising toluene and/or benzene is reacted with methanol under alkylation conditions in a reactor in the presence of a fluidized bed of solid catalyst particles to produce a vapor phase effluent comprising para-xylene, water, unreacted toluene and/or benzene and solid catalyst fines. The vapor phase effluent is contacted with a liquid hydrocarbon quench stream under conditions to condense a minor portion of the vapor phase effluent and produce a condensate which contains at least some of the catalyst fines and which is substantially free of an aqueous phase. The condensate containing said catalyst fines is then separated from the remainder of the vapor phase effluent.

17 Claims, 2 Drawing Sheets

PRODUCTION OF PARA-XYLENE BY THE METHYLATION OF BENZENE AND/OR TOLUENE

CROSS REFERENCE TO RELATED APPLICATIONS

This application claims the benefit of Provisional Application No. 61/253,745, filed Oct. 21, 2009, the disclosure of which is incorporated by reference in its entirety.

FIELD

This invention relates to a process for producing para-xylene by the selective methylation of benzene and/or toluene.

BACKGROUND

Para-xylene is an important starting material for manufacturing terephthalic acid, which is itself a valuable intermediate in the production of synthetic polyester fibers, films, and resins. These polyester materials have many practical, well known uses, such as in fabrics, carpets, and apparel.

One known route for the manufacture of para-xylene is by the methylation of benzene and/or toluene. For example, U.S. Pat. No. 6,504,072 discloses a process for the selective production of para-xylene which comprises reacting toluene with methanol under alkylation conditions in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa) wherein said porous crystalline material has undergone prior treatment with steam at a temperature of at least 950° C. to adjust the Diffusion Parameter of said material to about 0.1-15 $sec^{-1}$. The reaction can be carried out in a fixed, moving, or fluid catalyst bed.

In addition, U.S. Pat. No. 6,642,426 discloses a process for alkylating an aromatic hydrocarbon reactant, especially toluene, with an alkylating reagent comprising methanol to produce an alkylated aromatic product, comprising: introducing the aromatic hydrocarbon reactant into a reactor system at a first location, wherein the reactor system includes a fluidized bed reaction zone comprising a temperature of 500 to 700° C. and an operating bed density of about 300 to 600 $kg/m^3$, for producing the alkylated aromatic product; introducing a plurality of streams of said alkylating reactant directly into said fluidized bed reaction zone at positions spaced apart in the direction of flow of the aromatic hydrocarbon reactant, at least one of said streams being introduced at a second location downstream from the first location; and recovering the alkylate aromatic product, produced by reaction of the aromatic reactant and the alkylating reagent, from the reactor system.

The reaction of toluene and methanol, particularly using the highly steamed catalyst described in the '072 patent is highly selective to the production of para-xylene. However, in addition to para-xylene the reaction product contains water, as a necessary by-product of the substitution of a hydrogen group of the benzene ring by the methyl group of the methanol. Other side reactions generate small quantities of oxygenated organic species, many of which are organic acids, such as formic acid, acetic acid and alkyl phenols (such as, methyl, dimethyl and ethyl phenols). Thus the effluent from a toluene methylation reaction includes product xylene, unreacted toluene, light gas products, heavier aromatic species and an aqueous vapor phase. Where the reaction is conducted in a fluidized bed, such as disclosed in the '426 patent, the effluent will also contain catalysts fines which are not recovered by the catalyst separation system of the reactor. These catalysts fines mostly end up in the aqueous phase which, by virtue of the presence of the organic acids, has a low pH. Such an environment is conducive to partial dissolution of the catalyst fines rendering them "sticky" and difficult to separate from the water/oil mixture. This solids separation problem is accentuated by the fact that the solids are in low concentration requiring the processing of large volumes of liquid in the solids recovery step (such as, filtration).

There is therefore a need for an effective process for recovering catalyst fines from the reaction effluent of a fluid bed methylation process that avoids the processing of a low pH aqueous phase having a very dilute catalyst solids concentration. According to the invention, this is provided by contacting the reaction effluent vapor with a liquid hydrocarbon quench stream so as to condense a controlled, minor part of the effluent vapor and produce a condensate which contains at least some of the catalyst fines and which is substantially free of an aqueous phase. After concentration of the solids in the condensate, the catalyst fines can be recycled back to the methylation process preferably using a flush stream containing methanol and/or the aromatic reagent of the process, namely benzene or toluene.

SUMMARY

In one aspect, the invention resides in a process for the production of para-xylene, the process comprising:

(a) reacting an aromatic feedstock comprising toluene and/or benzene with methanol under alkylation conditions in a reactor in the presence of a fluidized bed of solid catalyst particles to produce a vapor phase effluent comprising para-xylene, water, unreacted toluene and/or benzene and solid catalyst fines;

(b) contacting the vapor phase effluent with a liquid hydrocarbon quench stream under conditions to condense a minor portion of the vapor phase effluent and produce a condensate which contains at least some of the catalyst fines and which is substantially free of an aqueous phase; and (c) separating the condensate containing said catalyst fines from the remainder of the vapor phase effluent.

Conveniently, said liquid hydrocarbon quench stream is contacted with said vapor phase effluent in countercurrent flow or alternatively in cocurrent flow.

Conveniently, said contacting condenses less than 10 weight %, such as less than 5 weight %, for example less than 2 weight %, of said vapor phase effluent.

Conveniently, said liquid hydrocarbon quench stream contains less than 1 volume % free water.

In one embodiment, said liquid hydrocarbon quench stream comprises at least part of the condensate separated in (c) and conveniently the process further includes:

(d) cooling the condensate containing said catalyst fines; and (e) recycling the cooled condensate to the contacting (b).

Preferably, the process still further includes:

(f) removing at least part of said catalyst fines from said condensate prior to said recycling (e).

(g) returning at least part of the catalyst fines removed from said condensate to said reacting (a).

Conveniently, the catalyst fines are returned to said reacting (a) by flushing with a liquid flush stream comprising said aromatic feedstock and/or methanol. Typically, the liquid flush stream contains less than 5 volume %, such as less than 2 volume %, for example 1 volume %, free water.

In one embodiment, the process further comprises:

(h) continuously removing part of said solid catalyst particles from said reactor and feeding said removed solid catalyst particles to a regenerator;

(i) contacting the catalyst particles in the regenerator with an oxygen-containing gas to remove coke therefrom and produce a flue gas effluent containing catalyst fines;

(j) continuously returning part of the solid catalyst particles in the regenerator to the reactor; and (k) purging catalyst fines from said flue gas effluent to control the level of catalyst fines in the reactor and the regenerator.

In one embodiment, the solid catalyst particles comprise a porous crystalline material, typically having a Diffusion Parameter for 2,2 dimethylbutane of about 0.1-15 sec$^{-1}$ when measured at a temperature of 120° C. and a 2,2 dimethylbutane pressure of 60 torr (8 kPa).

Conveniently, the porous crystalline material comprises an aluminosilicate zeolite, such as ZSM-5 or ZSM-11.

DETAILED DESCRIPTION

Figure 1:
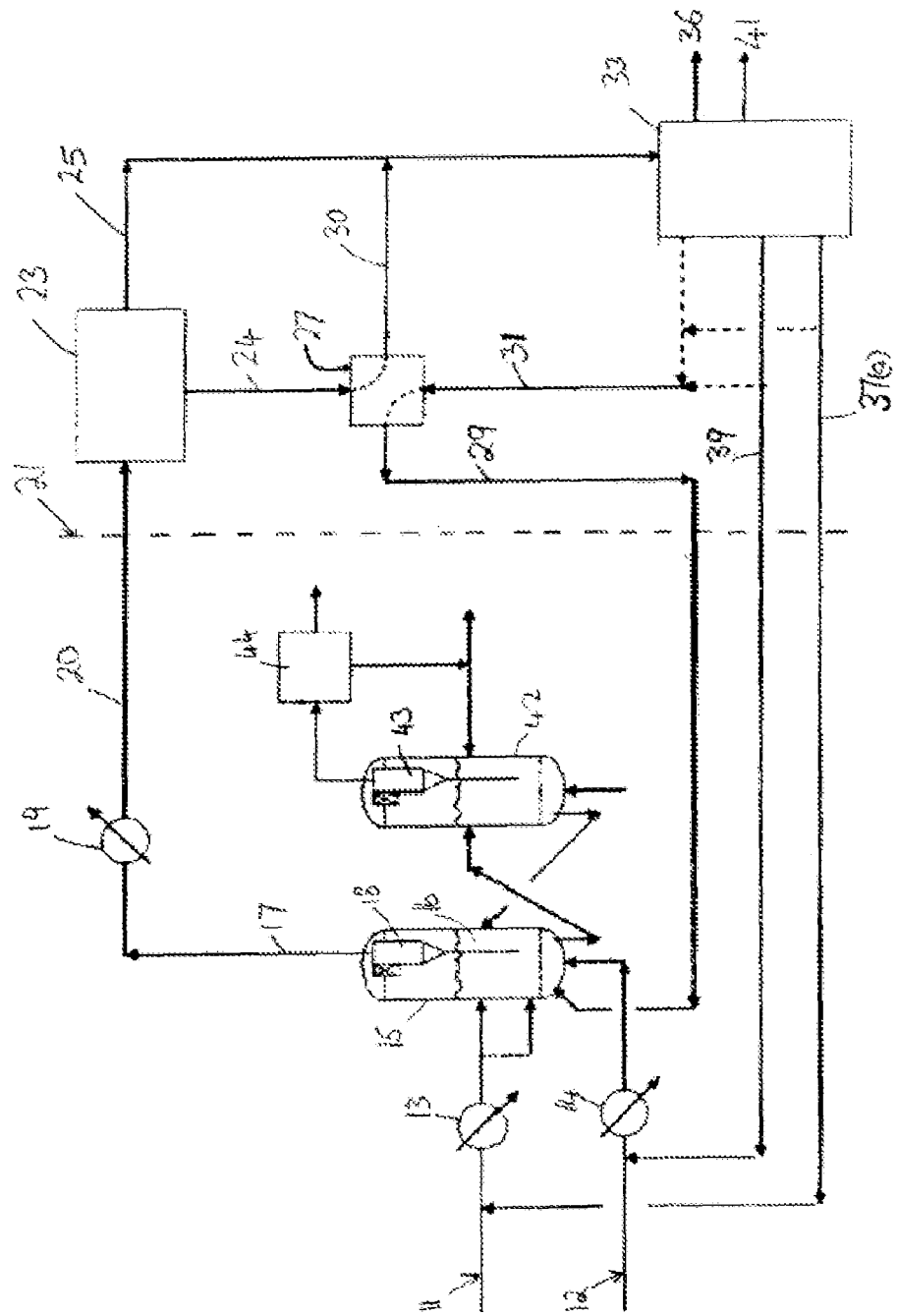
FIG. 1 is a flow diagram of a process for methylating toluene according to a one embodiment of the invention.

As used herein, the term "catalyst fines" means the small particles of catalytic material, generally having an average diameter of less than 20 microns, that are produced as a result of continued impact between the catalyst particles in the fluidized bed of catalyst employed in the present process.

As used herein the term "fluidized bed" means a zone or vessel wherein particulates contact with gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below about 95%. Description of the minimum fluidization velocity is given in, for example, Chapter 3 of "Fluidization Engineering," D. Kunii and O. Levenspiel, 2$^{nd}$ Edition, Butterworth-Heinemann, Boston, 1991 and Chapter 6 of "Chemical Process Equipment," S. M. Walas, Butterworth-Heinemann, Boston, 1990, the entirety of which are incorporated by reference.

The present invention relates to a process for producing para-xylene by reacting an aromatic feedstock comprising toluene and/or benzene with methanol under alkylation conditions in the presence of a fluidized bed of solid catalyst particles. The process produces a vapor phase effluent comprising the desired para-xylene, water, unreacted toluene and/or benzene and solid catalyst fines. To assist in separating the catalyst fines from the vapor phase effluent, the effluent is contacted with a liquid hydrocarbon quench stream so as to condense a minor portion of the vapor phase effluent and produce a condensate which contains at least some of the catalyst fines and which is substantially free of an aqueous phase. After separating the resulting condensate from the remainder of the vapor phase effluent, the catalyst fines are generally removed, possibly for recycling to the alkylation step, and, after cooling, the condensate can be recycled quench step.

Alkylation Process

The alkylation process employed herein can employ any aromatic feedstock comprising toluene and/or benzene, although in general it is preferred that the aromatic feed contains at least 90 weight %, especially at least 99 weight %, of benzene, toluene or a mixture thereof. An aromatic feed containing at least 99 weight % toluene is particularly desirable.

Similarly, although the composition of the methanol-containing feed is not critical, it is generally desirable to employ feeds containing at least 90 weight %, especially at least 99 weight %, of methanol.

The catalyst employed in the present process is a porous crystalline material, typically having a Diffusion Parameter for 2,2 dimethylbutane of about 0.1-15 sec$^{-1}$ when measured at a temperature of 120° C. and a 2,2 dimethylbutane pressure of 60 torr (8 kPa).

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_{1.3}$, where $Q_{1.3}$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described U.S. Pat. No. 4,076,842. Zeolite ZSM-35 and the conventional preparation thereof are described in U.S. Pat. No. 4,016,245. ZSM-48 and the conventional preparation thereof is taught by U.S. Pat. No. 4,375,573. The entire disclosures of these U.S. patents are incorporated herein by reference.

The medium pore zeolites described above are preferred for the present process since the size and shape of their pores favor the production of p-xylene over the other xylene isomers. However, conventional forms of these zeolites have Diffusion Parameter values in excess of the 0.1-15 sec$^{-1}$ range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is derived by measuring the n-hexane adsorption capacity of the zeolite, before and after steaming, at 90° C. and 75 torr n-hexane pressure.

Steaming of the porous crystalline material is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Most preferably, said at least one oxide modifier is selected from oxides of boron, magnesium, calcium, lanthanum and most preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt. %, and preferably is between about 0.1 and about 10 wt. %, based on the weight of the final catalyst.

Where the modifier includes phosphorus, incorporation of modifier in the catalyst of the invention is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours.

Representative phosphorus-containing compounds which may be used to incorporate a phosphorus oxide modifier into the catalyst of the invention include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$ and secondary, $R_2P(O)OX$, phosphonic acids. such as benzene phosphonic acid, the corresponding sulfur derivatives such as $RP(S)(SX)_2$ and $R_2P(S)SX$, the esters of the phosphonic acids, such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

Representative boron-containing compounds which may be used to incorporate a boron oxide modifier into the catalyst of the invention include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the present process may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt. % of the composite.

In one embodiment, the binder material comprises silica or a kaolin day. Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

In the present process, the methanol and aromatic feeds are contacted with the catalyst described above with the catalyst particles being disposed in one or more fluidized beds. Each of the methanol and aromatic feeds can be injected into the fluidized catalyst in a single stage. However, in a preferred embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

Irrespective of the disposition of the catalyst, as the reaction proceeds the catalyst gradually deactivates as a result of build-up of carbonaceous material, generally referred to as "coke" on the catalyst. Thus, a portion of the catalyst in the or each fluidized bed is generally withdrawn, either on a continuous or a periodic basis, and fed to a separate regenerator. In the regenerator, the catalyst, again in the form of a fluidized bed, is contacted with an oxygen-containing gas, such as air, at a temperature between about 400 and about 700° C. so as to burn off the coke and regenerate the catalyst. The regenerated catalyst is continuously or periodically returned to the alkylation reactor, whereas the exhaust gas from the regenerator is scrubbed to remove entrained catalyst fines. The separated fines can be returned to the regenerator and/or purged to control the build-up of fines in the catalyst inventory.

The conditions employed in the alkylation stage of the present process are not narrowly constrained but, in the case of the methylation of toluene, generally include the following ranges: (a) temperature between about 500 and about 700° C., such as between about 500 and about 600° C.; (b) pressure of between about 1 atmosphere and about 1000 psig (between about 100 and about 7000 kPa), such as between about 10 psig and about 200 psig (between about 170 and about 1480 kPa); (c) moles toluene/moles methanol (in the reactor charge) of at least about 0.2, and preferably from about 0.2 to about 20; and (d) a weight hourly space velocity ("WHSV") for total hydrocarbon feed to the reactor(s) of about 0.2 to about 1000, preferably about 0.5 to about 500 for the aromatic reactant, and about 0.01 to about 100 for the combined methanol reagent stage flows, based on total catalyst in the reactor(s).

Product Treatment and Recovery

The product of the reaction between the methanol and aromatic feeds is a gaseous effluent comprising para-xylene, water vapor, unreacted toluene and/or benzene, unreacted methanol, light olefins and other light gas by-products, generally some $C_9+$ aromatic by-products and entrained solid catalyst and catalyst fines. Thus the gaseous effluent leaving the (final) fluidized bed reactor is generally passed through an integral cyclone separator to remove some of the entrained catalyst solids and return them to the alkylation reactor. However, even after passage through the cyclone separator, the product effluent still inevitably contains some solid catalyst fines and the present process provides a simple and efficient process of removing the catalyst fines from the product effluent and recycling the fines back to the methylation step.

The product effluent leaves the fluidized bed reactor system at a high temperature, typically between about 500 and about 600° C., and initially may be passed through a heat exchanger so that the waste heat in the effluent stream may be recovered and used to heat other process stream(s). It is, however, preferred that any initial cooling of the product stream is limited so as to keep the effluent vapors well above the dew point, typically about 240° F. (116° C.). Conveniently, the temperature of the effluent after waste heat recovery is between about 150 and about 500° C.

Following initial cooling, the effluent vapor stream is subjected to a quench step in which the effluent is contacted with liquid hydrocarbon quench stream to further cool and partially condense the effluent. The quantity and temperature of the liquid hydrocarbon quench stream are controlled so that only a minor portion of the effluent stream, typically less than 10 weight %, such as less than 5 weight %, for example less than 2 weight %, of the effluent stream is condensed. The resulting condensate, made up of the hydrocarbon quench stream plus the condensed effluent including some of the catalyst fines, are separated from the vapor and, by controlling the amount of effluent condensed in the quench step, it is found that the condensate is substantially free of a separate water phase. It is to be understood that the condensate will contain some quantity of dissolved water, but should not contain any free water (as evidenced by either a cloudy appearance of the condensate or by the appearance of a phase separation upon standing). This is important since the presence of a separate water phase will make concentration of the solid catalyst fines from the condensate more difficult.

The liquid hydrocarbon used for the quench step should generally contain less than 1 volume % free water and preferably no visible free water. Apart from this the liquid hydrocarbon used for the quench step can be any aliphatic or aromatic hydrocarbon having from 6 to 12 carbon atoms. It is, however, generally preferred to employ a hydrocarbon from within the process, particularly some or all of the condensate from the quench step. In the latter case, the quench oil may or may not contain catalyst fines. In one embodiment, the condensate from the quench step is used as the quench oil by recirculating the condensate through a cooler to control the heat removed, without separating the catalyst fines from the condensate. Alternatively, at least a portion of the condensate may undergo processing to remove solid material. This "solids-free" condensate may be used advantageously to "scrub" the vapor from the quench step to further reduce any solids entrainment with the vapor product.

The quench step should be designed to maximize the solids removal efficiency from the effluent vapor and into the condensate. This may be achieved using a column with the liquid hydrocarbon quench stream circulating through the column countercurrent to the effluent vapor stream. The column typically contains internals, such as trays or packing, to maximize the contacting area between the vapor and liquid phases. Alternatively, a single stage scrubber may be used, such as a venturi scrubber, to contact the liquid hydrocarbon quench stream with the effluent vapor. This device is typically co-current, with liquid and vapor flowing in the same direction. A high degree of contacting is achieved through intense mixing of fine liquid drops with the vapor stream in a high-velocity zone. With this alternative, a downstream separator is used to separate the vapor from the solids-containing liquid.

The net liquid removed from the quench step contains catalyst fines in a much higher concentration than would be found from cooling of the complete effluent stream approaching ambient. In addition, this concentrated solids-in-oil stream does not contain any free water. The stream may, however, undergo or more processing step to further concentrate the solids. Various means are available for this additional solids concentration, including but not limited to filtration, settling and electrostatic precipitation.

It may be desirable to return the concentrated catalyst fines to the methylation step, in order to reduce catalyst losses and to improve the fluidization properties in the fluid bed reactor. Conveniently, the concentrated catalyst fines are returned to the reactor as a slurry in a liquid flush stream. Typically, the flush stream comprises the aromatic feedstock and/or methanol, such as at least 90 volume % aromatic feedstock plus methanol and less than 5 volume %, such as less than 2 volume %, for examples less than 1 volume %, free water. In one embodiment, the flush stream comprises a sidestream from the detoluenizer column in the downstream separation process.

After subjecting the gaseous reactor effluent to the quench step and separating the condensate thereby generated, the remaining gaseous effluent is typically at a temperature between about 100 and about 150° C. The remaining effluent is then cooled further, typically to a temperature between about 25 and about 70° C., and fed to a three-phase separator where the effluent separates into a liquid organic phase rich in the aromatic components of the effluent, a liquid aqueous phase containing most of unreacted methanol and a gaseous phase containing most of the light gas by-products. The organic phase is recovered from the separator and passed to a first distillation column, the detoluenizer column, to remove the unreacted toluene and then to a second distillation column to remove the $C_9+$ aromatic by-products and recover the p-xylene product.

Figure 2:
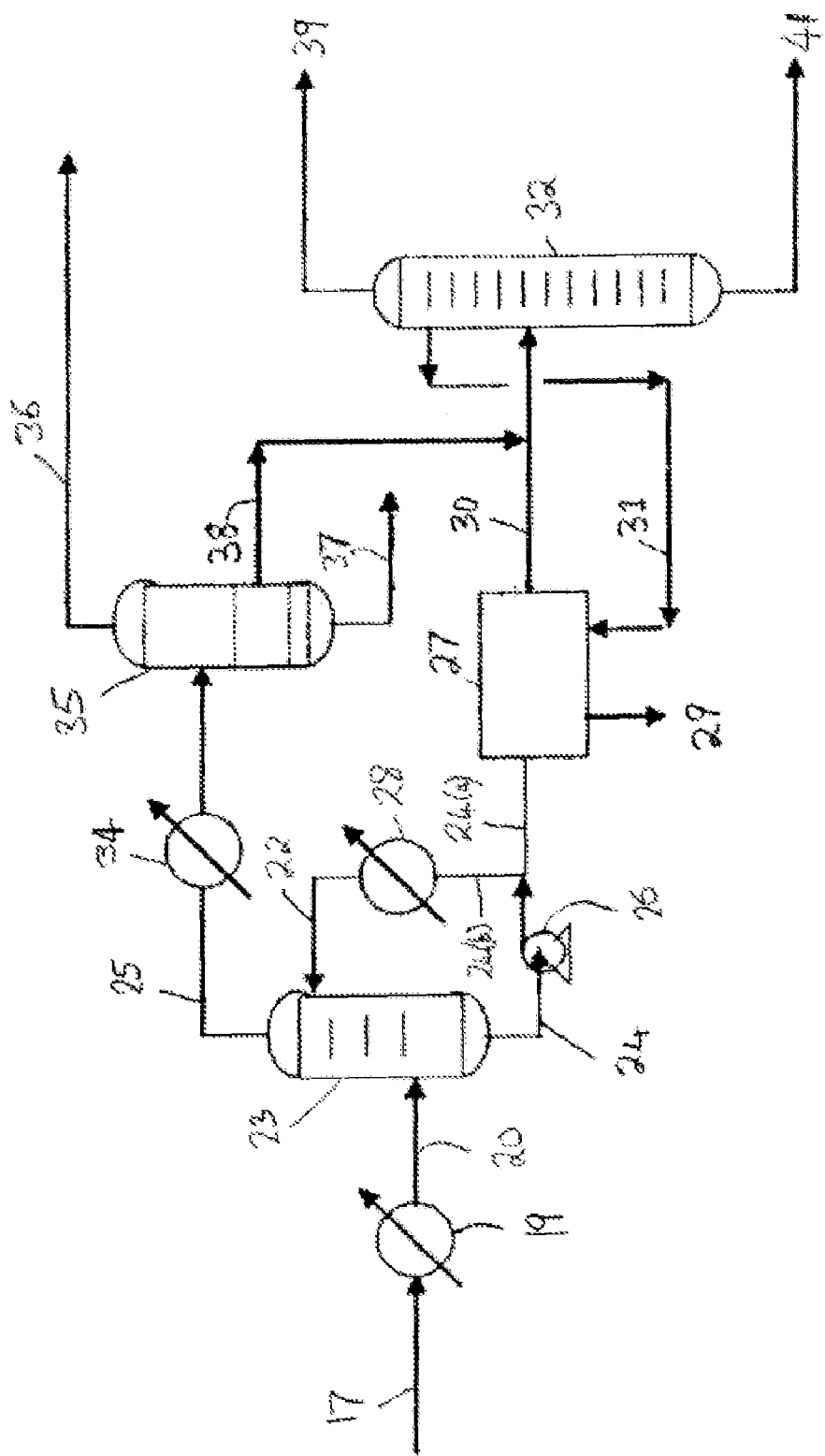
FIG. 2 is a flow diagram of part of the product treatment and recovery stages of the process shown in FIG. 1.

One embodiment of a process for producing para-xylene by the reaction of methanol with toluene will now be more particularly described with reference to the accompanying drawings, in which FIG. 1 illustrates the overall process and FIG. 2 illustrates part of product treatment and recovery stages of the process.

Referring initially to FIG. 1, methanol and toluene feeds 11, 12 respectively are passed through heaters 13, 14 respectively and supplied to a vertically disposed reactor 15 containing a fluidized bed of catalyst 16. The heated toluene feed 12 is supplied to the base of the reactor 15, whereas the heated methanol feed is split and supplied to reactor 15 at a plurality of vertically spaced locations above the base of the reactor. The methanol and toluene react in the reactor 15 to produce a gaseous product effluent 17 which contains entrained catalyst solids. The effluent is therefore initially passed through a cyclone separator 18 to remove part of the catalyst solids and return them to the fluidized bed 16. On leaving the reactor 15, the gaseous effluent 17 contains the desired para-xylene, water vapor, unreacted toluene and methanol, light gas by-products, $C_9+$ aromatic by-products and a small amount, generally less than 0.5 weight %, of solid catalyst fines which were not removed by the cyclone separator 18.

The gaseous effluent 17 is initially passed through a heat exchanger 19 where waste heat is recovered and the cooled effluent stream 20 is then passed to a product treatment and recovery section illustrated generally at 21 in FIG. 1 and shown in more detail in FIG. 2. The first stage of product treatment and recovery involves contacting the gaseous effluent with a liquid hydrocarbon quench stream 22 (FIG. 2) in a quench column 23 so as to cool and partially condense the effluent to produce a liquid condensate stream 24 and a gaseous product stream 25.

The liquid condensate stream 24 is substantially free of an aqueous phase and contains most of the catalyst fines entrained in the gaseous effluent 17. A pump 26 removes the liquid condensate stream 24 from the quench column 23 and feeds a first part 24(a) of the stream 24 to a solids concentration unit 27 and a second part 24(b) to a heat exchanger 28 where the second part of the condensate stream is cooled to produce the quench stream 22. Stream 24(a) is the "net" condensate produced from the quench step. The catalyst fines in the stream 24(a) are concentrated in the unit 27, for example by filtration, electrostatic precipitation or centrifuging. After concentration of fines in unit 27, the "net" condensate stream leaves the unit as stream 30, which is substantially free of catalyst fines. Optionally, the fines concentrated in unit 27 can be removed from the unit as an outlet stream 29 by washing with a toluene flush stream 31. As shown in FIG. 1, the catalyst-containing outlet stream 29 is then recycled to the reactor 15. Alternately, the concentrated catalyst fines can be removed from unit 27 without washing or flushing with a flush stream. After removal of the catalyst fines, stream 30 is fed to a detoluenizer column 32 which forms part of the product recovery section illustrated generally at 33 in FIG. 1.

Referring now to FIG. 2, after leaving the quench column 23, the gaseous product stream 25 is cooled in a heat exchanger 34 and passed to a three-phase separator 35 where the effluent separates into a liquid organic phase rich in the aromatic components of the effluent, a liquid aqueous phase containing most of unreacted methanol and a gaseous phase containing most of the light gas by-products. The gaseous phase is removed from the separator 35 as an overhead stream 36, which can be treated to separate the light olefins and other useful light gas by-products, whereas the liquid aqueous phase is removed as a recycle steam 37, from which the methanol is recovered and recycled to the reactor 15 (see stream 37a in FIG. 1). The liquid organic phase is removed from the separator 35 as a product steam 38 and is combined with the fines-free first part of the condensate, stream 30, and fed to the detoluenizer column 32. The column 32 separates the combined product stream into a toluene-rich overhead stream 39, which is recycled to the reactor 15, and a bottoms stream 41 containing the para-xylene product together with any $C_9+$ by-products. The bottoms stream 41 is fed to a further distillation unit (not shown) to separate the desired para-xylene product from the heavier aromatic by-products. The heavier aromatic by-products can optionally be recycled as make-up to the liquid hydrocarbon quench stream 22.

As shown in FIG. 1, part of the catalyst in the reactor 16 is periodically or continuously regenerated in a regenerator 42 and the exhaust gas from the regenerator is passed through a cyclone separator 43 to remove catalyst fines. The fines are collected in a recovery unit 44, and are optionally recycled to the regenerator 42 and/or purged. By purging the catalyst fines recovered from the regenerator effluent, rather than from the product effluent 17, it is possible to ensure that the purged fines are substantially free, that is contain less than 10 wppm, such as less than 5 wppm, for example less than 1 wppm, of aromatic contamination.

In a modification of the process shown in FIGS. 1 and 2, the solids concentration unit 27 could be omitted and the first part 24(a) of the condensate stream be fed directly to the detoluenizer column 32. In this option, the solids go to the bottom of the column 32, and eventually leave with the heavy oil byproduct stream 41. At this point, they can either be left in the stream for a fuel application (if solids are within specification limits), or they can be filtered out at that point, where the flow rate is very small.

The invention will now be more particularly described with reference to the following non-limiting Example.

Example

This example describes a computer simulation of the process for producing para-xylene disclosed in FIGS. 1 and 2. The results of the simulation are summarized in Table 1 below.

The reactor effluent 17 is at a temperature of 590° C. and a pressure of 40 psia (276 kPa). Waste heat is recovered in the heat exchanger 19, cooling the effluent to 204° C. (400° F.) with pressure drop of 5 psi (34 kPa). The quench step is simulated as a 3-stage quench column with oil recirculation, with the duty of the quench step being controlled to produce just a small amount of net oil production in the condensate stream 24 produced by the quench column 23. In the simulation, the net oil make in the condensate stream 24 is less than 2% of the total mass flow of the reactor effluent 17. The temperature of the condensate stream 24 is 248° F. (120° C.) and of the overhead stream 25 is 234° F. (112° C.). The dew point of the effluent is about 240° F. (116° C.) and a free water phase is reached at a temperature of about 224° F. (107° C.). This means that the quench step can operate at least 20° F. (11° C.) away from the temperature where a free water phase would exist in the quench separator 23.

In addition to paraxylene, the process according to the present invention can be used to produce toluene (from benzene), other C7+ products such as ortho- and metaxylene, along with side products including light olefins such as ethylene, propylene, butylene isomers, pentene, hydrogen, methane, ethane, butane, pentane, butadiene, and the like. Accordingly, while the present invention is directed most specifically to the preferred embodiment of the production of paraxylene, one of skill in the art would recognize that through routine experimentation the process of the invention can be optimized for the production of one of the other products set forth herein.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

TABLE 1

| | | Stream Ref No. | | | | | | |
|---|---|---|---|---|---|---|---|---|
| | Units | 17 | 20 | 25 | 24 | 24(b) | 24(a) | 22 |
| Phase | | Vapor | Vapor | Vapor | Liquid | Liquid | Liquid | Liquid |
| Temperature | ° F. | 1100.00 | 400.00 | 238.42 | 247.85 | 247.85 | 247.85 | 233.00 |
| Pressure | PSIA | 35.00 | 30.00 | 30.00 | 30.00 | 30.00 | 30.00 | 30.00 |
| Total M.W. | | 49.480 | 49.480 | 49.014 | 97.673 | 97.673 | 97.673 | 97.673 |
| Molar Rate | Lb-mol/hr | 27.41 | 27.41 | 27.16 | 137.31 | 137.06 | 0.26 | 137.06 |
| Mass Rate | Lb/hr | 1356.3 | 1356.3 | 1331.0 | 13411.7 | 13386.6 | 25.1 | 13386.6 |
| Total molar comp. rates | Lb-mol/hr | | | | | | | |
| Methane | | 0.935 | 0.935 | 0.935 | 0.020 | 0.020 | 0.000 | 0.020 |
| Ethene | | 0.545 | 0.545 | 0.545 | 0.032 | 0.032 | 0.000 | 0.032 |
| Xylene | | 7.721 | 7.721 | 7.608 | 70.459 | 70.327 | 0.132 | 70.327 |
| 14DMBenzene | | 3.064 | 3.064 | 2.945 | 59.198 | 59.087 | 0.111 | 59.087 |
| 124TMBenzene | | 0.077 | 0.077 | 0.064 | 3.252 | 3.246 | 0.006 | 3.246 |
| 1M3EBenzene | | 0.044 | 0.044 | 0.039 | 1.547 | 1.544 | 0.003 | 1.544 |
| Methanol | | 0.293 | 0.293 | 0.293 | 0.438 | 0.437 | 0.001 | 0.437 |
| H2O | | 14.732 | 14.732 | 14.727 | 2.366 | 2.362 | 0.004 | 2.362 |
| Total molar comp. fractions | | | | | | | | |
| Methane | | 0.0344110 | 0.0344110 | 0.034429 | 0.000147 | 0.000147 | 0.000147 | 0.000147 |
| Ethene | | 0.019896 | 0.019896 | 0.020081 | 0.000234 | 0.000234 | 0.000234 | 0.000234 |
| Xylene | | 0.281667 | 0.281667 | 0.280145 | 0.513130 | 0.513130 | 0.513130 | 0.513130 |
| 14DMBenzene | | 0.111780 | 0.111780 | 0.108451 | 0.431118 | 0.431118 | 0.431118 | 0.431118 |
| 124TMBenzene | | 0.002792 | 0.002792 | 0.002360 | 0.023684 | 0.023684 | 0.023684 | 0.023684 |
| 1M3EBenzene | | 0.001609 | 0.001609 | 0.001440 | 0.011265 | 0.011265 | 0.011265 | 0.011265 |
| Methanol | | 0.010702 | 0.010702 | 0.010772 | 0.003189 | 0.003189 | 0.003189 | 0.003189 |
| H2O | | 0.537443 | 0.537443 | 0.542322 | 0.017233 | 0.017233 | 0.017233 | 0.017233 |
| Weight comp. fractions | | | | | | | | |
| Methane | | 0.011060 | 0.011060 | 0.011269 | 0.000024 | 0.000024 | 0.000024 | 0.000024 |
| Ethene | | 0.011281 | 0.011281 | 0.011494 | 0.000067 | 0.000067 | 0.000067 | 0.000067 |

TABLE 1-continued

| | Units | 17 | 20 | 25 | 24 | 24(b) | 24(a) | 22 |
|---|---|---|---|---|---|---|---|---|
| MBenzene | | 0.524515 | 0.524515 | 0.526637 | 0.484065 | 0.484065 | 0.484065 | 0.484065 |
| 14DMBenzene | | 0.239844 | 0.239844 | 0.234910 | 0.468612 | 0.468612 | 0.468612 | 0.468612 |
| 124TMBenzene | | 0.006783 | 0.006783 | 0.005787 | 0.029146 | 0.029146 | 0.029146 | 0.029146 |
| 1M3EBenzene | | 0.003908 | 0.003908 | 0.00.530 | 0.013862 | 0.013862 | 0.013862 | 0.013862 |
| Methanol | | 0.006931 | 0.006931 | 0.007042 | 0.001046 | 0.001046 | 0.001046 | 0.001046 |
| H2O | | 0.195679 | 0.195679 | 0.199332 | 0.003178 | 0.003178 | 0.003178 | 0.003178 |
| Total density | Lb/ft3 | 0.104 | 0.164 | 0.205 | 48.178 | 48.178 | 48.178 | 48.691 |
| Vapor viscosity | Cp | 0.02329 | 0.01321 | 0.01072 | n/a | n/a | n/a | n/a |
| Liquid viscosity | Cp | n/a | n/a | n/a | 0.23839 | 0.23839 | 0.23839 | 0.25422 |

The invention claimed is:

1. A process for the production of para-xylene, the process comprising:
    (a) reacting an aromatic feedstock comprising toluene and/or benzene with methanol under alkylation conditions in a reactor in the presence of a fluidized bed of solid catalyst particles comprising ZSM-5 or ZSM-11 zeolites to produce a vapor phase effluent comprising paraxylene, water, unreacted toluene and/or benzene and solid catalyst fines;
    (b) contacting the vapor phase effluent with a liquid hydrocarbon quench stream under conditions to condense a minor portion of the vapor phase effluent and produce a condensate which contains at least some of the catalyst fines and which is substantially free of an aqueous phase; and
    (c) separating the condensate containing said catalyst fines from the remainder of the vapor phase effluent.

2. The process of claim 1, wherein said liquid hydrocarbon quench stream is contacted with said vapor phase effluent in countercurrent flow.

3. The process of claim 1, wherein said liquid hydrocarbon quench stream is contacted with said vapor phase effluent in cocurrent flow.

4. The process of claim 1, wherein said contacting condenses less than 10 weight % of said vapor phase effluent.

5. The process of claim 1, wherein said contacting condenses less than 5 weight % of said vapor phase effluent.

6. The process of claim 1, wherein said contacting condenses less than 2 weight % of said vapor phase effluent.

7. The process of claim 1, wherein said liquid hydrocarbon quench stream contains less than 1 volume % free water.

8. The process of claim 1, wherein said liquid hydrocarbon quench stream comprises at least part of the condensate separated in (c).

9. The process of claim 8 and further including:
    (d) cooling the condensate containing said catalyst fines; and
    (e) recycling the cooled condensate to the contacting (b).

10. The process of claim 9 and further including:
    (f) removing at least part of said catalyst fines from said condensate prior to said recycling (e).

11. The process of claim 10 and further including:
    (g) returning at least part of the catalyst fines removed from said condensate to said reacting (a).

12. The process of claim 11, wherein said catalyst fines are returned to said reacting (a) by flushing with a liquid flush stream comprising said aromatic feedstock and/or methanol.

13. The process of claim 12, wherein said liquid flush stream contains less than 5 volume % free water.

14. The process of claim 12, wherein said liquid flush stream contains less than 2 volume % free water.

15. The process of claim 12, wherein said liquid flush stream contains less than 1 volume % free water.

16. The process of claim 1 and further including:
    (h) continuously removing part of said solid catalyst particles from said reactor and feeding said removed solid catalyst particles to a regenerator;
    (i) contacting the catalyst particles in the regenerator with an oxygen-containing gas to remove coke therefrom and produce a flue gas effluent containing catalyst fines;
    (j) continuously returning part of the solid catalyst particles in the regenerator to the reactor; and
    (k) purging catalyst fines from said flue gas effluent to control the level of catalyst fines in the reactor and the regenerator.

17. A process comprising:
    (a) reacting an aromatic feedstock comprising toluene and/or benzene with methanol under alkylation conditions in a reactor in the presence of a fluidized bed of solid catalyst particles comprising a porous crystalline material comprising ZSM-5 to produce a vapor phase effluent comprising paraxylene, water, unreacted toluene and/or benzene and solid catalyst fines;
    b) contacting the vapor phase effluent with a liquid hydrocarbon quench stream under conditions to condense a minor portion of the vapor phase effluent and produce a condensate which contains at least some of the catalyst fines and which is substantially free of an aqueous phase; and
    (c) separating the condensate containing said catalyst fines from the remainder of the vapor phase effluent.

* * * * *